US00PP18224P3

(12) United States Plant Patent

Goffreda et al.

(10) Patent No.: US PP18,224 P3

(45) Date of Patent: Nov. 20, 2007

(54) PEACH TREE NAMED 'NJ351'

(50) Latin Name: ***Prunus persica* L.**
Varietal Denomination: NJ351

(75) Inventors: Joseph C. Goffreda, Manalapan, NJ (US); Anna M. Voordeckers, East Windsor, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 11 days.

(21) Appl. No.: 11/333,491

(22) Filed: Jan. 17, 2006

(65) Prior Publication Data

US 2007/0169238 P1 Jul. 19, 2007

(51) Int. Cl.
*A01H 5/00* (2006.01)

(52) U.S. Cl. ..... Plt./198

(58) Field of Classification Search ..... Plt./198
See application file for complete search history.

*Primary Examiner*—Kent Bell
*Assistant Examiner*—Annette H Para
(74) *Attorney, Agent, or Firm*—James A. Lucas; Driggs, Hogg & Fry Co., L.P.A.

(57) ABSTRACT

A new and distinct peach variety of *Prunus persica* named 'NJ351' is provided. This variety is distinguished from other peach varieties by its unique combination of nonshowy flowers, fruit that ripen in late-midseason, attractively blushed fruit with a bright golden-yellow ground color, freestone fruit with a juicy, nearly nonmelting texture and sweet, low acid flavor, firm fruit that retain their firmness well and trees with regular, heavy production of fruit.

6 Drawing Sheets

Latin name of genus and species of the plant claimed: *Prunus persica* L.

BACKGROUND OF THE INVENTION

The present invention relates to a new and distinct variety of peach tree named 'NJ351'. Our new tree resulted from crossing 'NJ304' as the seed parent with 'J19-19-862144' peach tree, as the pollen parent. The new variety differs from seed parent 'NJ304' (unpatented) in that the new variety has firm fruit with yellow flesh while the parent has soft fruit with white flesh. The new variety differs from pollen parent 'J19-19-862144' (unpatented) in that the new variety has fruit with a bright ground color and yellow flesh, while the parent has fruit with a slight green ground color and white flesh. The resulting tree was selected when growing in a cultivated area as the 34$^{th}$ tree in the 40$^{th}$ row of Block K in Cream Ridge, N.J.

BRIEF SUMMARY OF THE INVENTION

The 'NJ351' variety is distinguished from other peach varieties due to the following unique combination of characteristics: Fruit with an attractive red skin color.

Fruit with a bright golden-yellow ground color.

Fruit with a sweet, low acid flavor.

Very firm fruit that retain their firmness well.

Regular and heavy production of fruit.

The variety was asexually reproduced at the Rutgers Fruit Research and Extension Center in Cream Ridge, N.J. Asexual reproduction of this new variety by budding onto 'Lovell' rootstock (unpatented) shows that the foregoing characteristics are so reproduced.

The following detailed description concerns the original tree, 'NJ351'. The original tree and progeny have been observed growing in a cultivated area in Cream Ridge, N.J.

Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
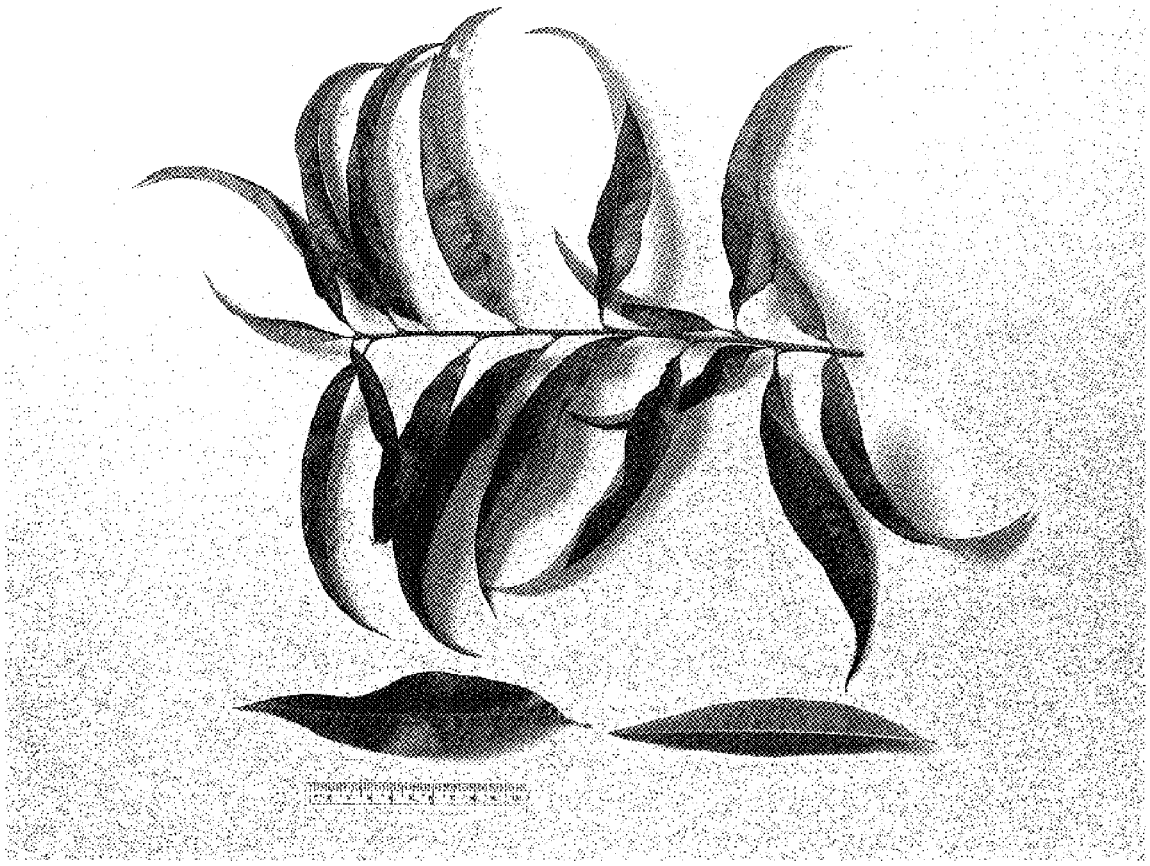
FIG. 1 is a color photograph taken on Aug. 29, 2005 of a characteristic twig of 'NJ351' in late summer bearing typical leaves of the mature foliage.
Figure 2:
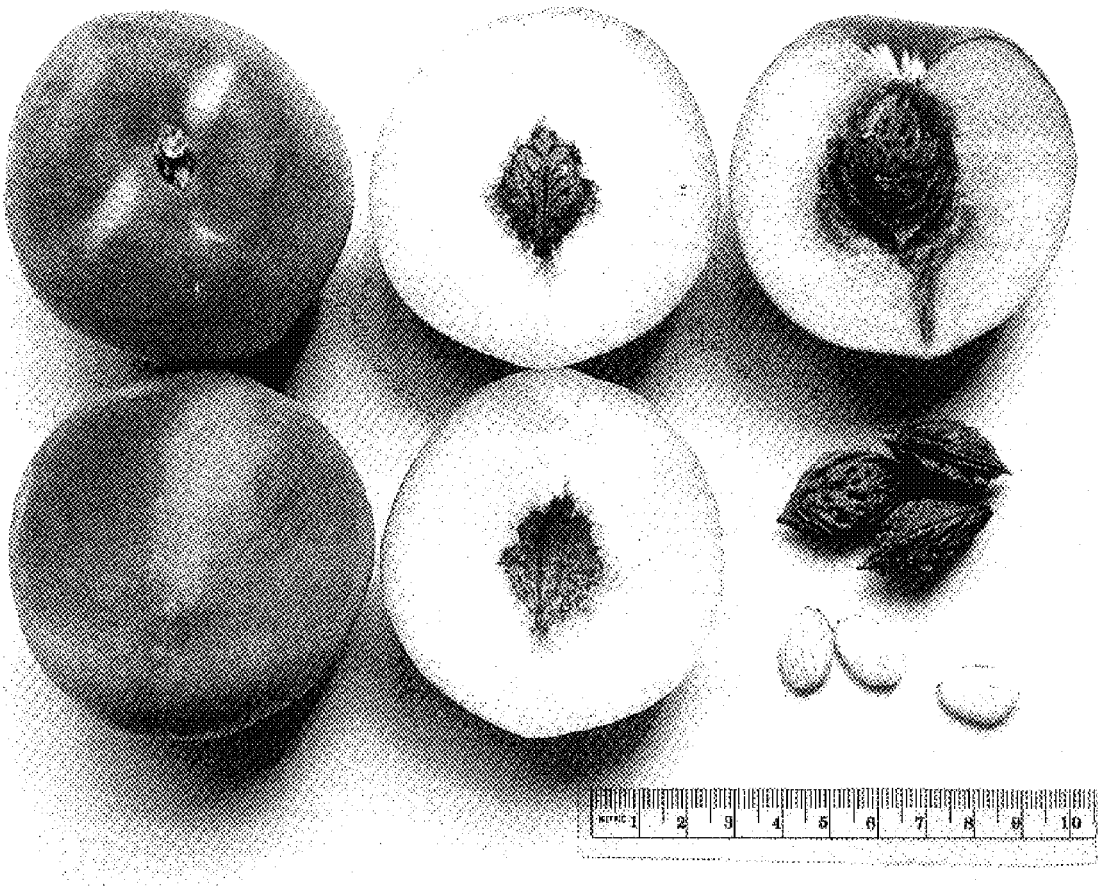
FIG. 2 is a color photograph of mature fruit of 'NJ351' and stones harvested in Cream Ridge, N.J. on Aug. 29, 2005. Whole fruit are presented in two positions and transverse and longitudinal cross sections to show that the pericarp comes free from the pit when the fruit is mature. The stones illustrate the medium, narrow dorsal ridge on the stone and the chains of pits forming grooves on the surface of the stone.
Figure 3:
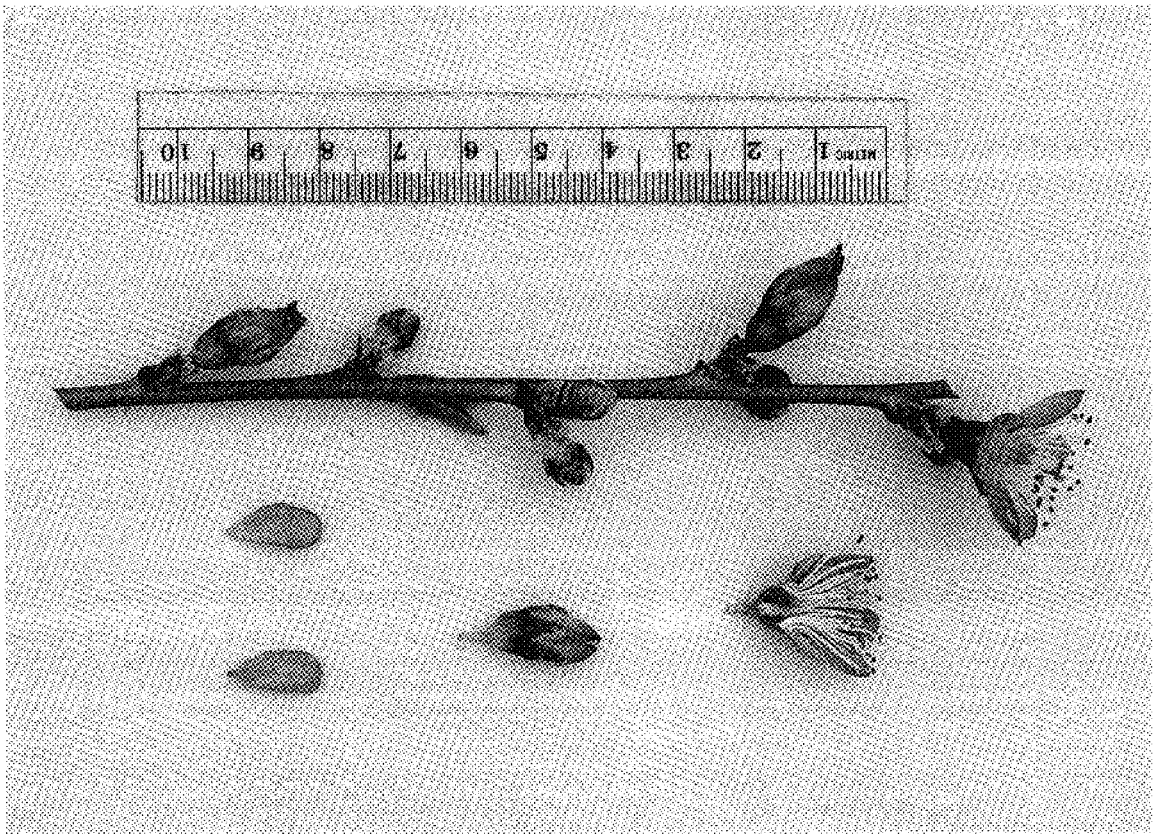
FIG. 3 is a color photograph of a characteristic twig that illustrates the typical flower buds and small, non showy flowers of 'NJ351' observed on a tree in Cream Ridge, N.J. on Apr. 21, 2004.
Figure 4:
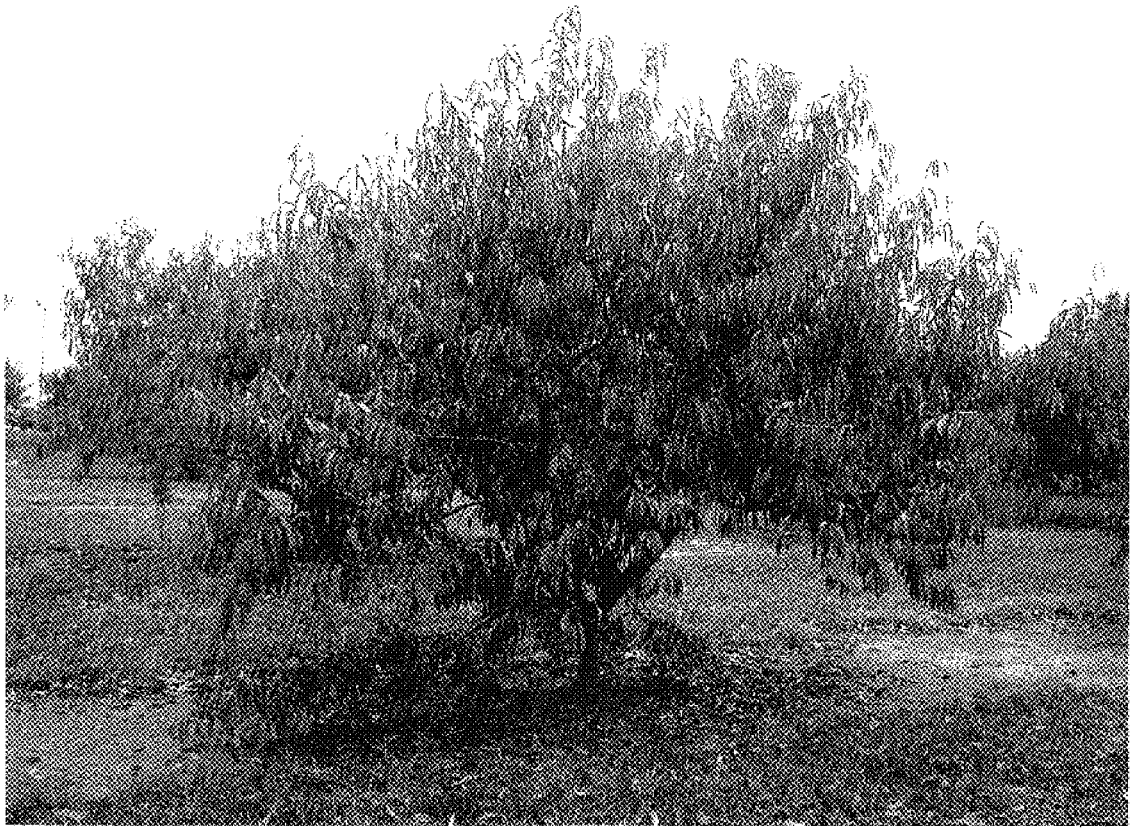
FIG. 4 is a color photograph of a tree of 'NJ351' in early fall that illustrates the spreading growth habit of a tree in Cream Ridge, N.J. on Oct. 27, 2005.
Figure 5:
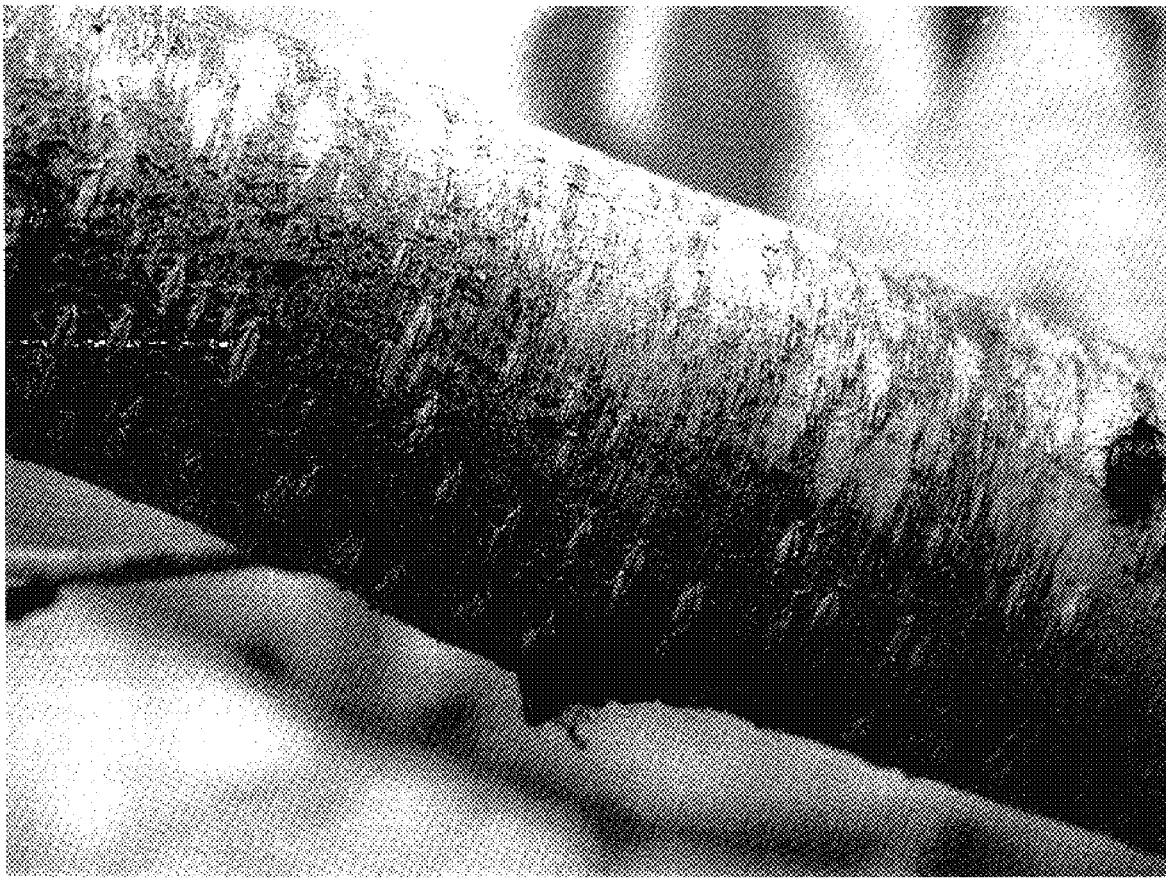
FIG. 5 is a color photograph taken on Oct. 27, 2005 of immature bark of 'NJ351' that illustrates color and the moderate density of elongated lenticels on the immature bark.
Figure 6:
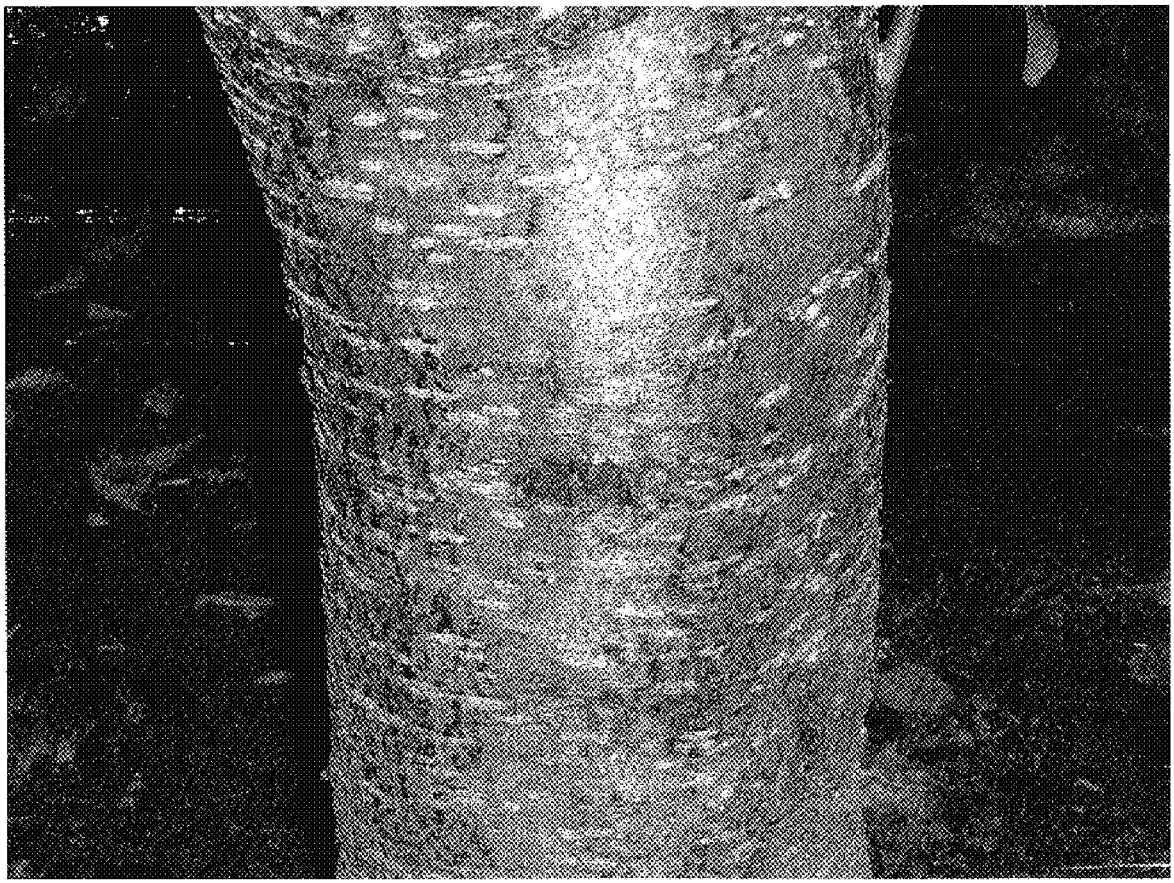
FIG. 6 is a color photograph taken on Oct. 27, 2005 of mature bark of 'NJ351' that illustrates the fairly smooth texture and prominent lenticels of the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ351' variety is based on observations of the original seedling tree. The observed tree was seven years of age and growing on 'Lovell' seedling rootstock (unpatented) in Cream Ridge, N.J.

Scientific name: *Prunus persica* L.
Parentage:

| | |
|---|---|
| Seed parent: | NJ304 |
| Pollen parent: | J19-19-862144 |

Tree:

| | |
|---|---|
| Vigor: | Moderately vigorous. |
| Plant hardiness zone: | Growth of plants has only been observed in zone 6b. |
| Dormant flower bud cold tolerance: | At least to −16° C. |
| Overall shape: | Spreading. |
| Height: | Below average as compared to other peach cultivars. For example, measurement of a typical grafted tree on 'Lovell' seedling rootstock (unpatented) at five years after planting shows an average height of 3.2 meters when grown in Cream Ridge, New Jersey. |
| Width | Average as compared to other peach cultivars. For example, measurement of a typical grafted tree on 'Lovell' seedling rootstock (unpatented) at five years after planting shows an average width of 5.3 meters when grown in Cream Ridge, New Jersey. |
| Caliper: | Five year old tree is 40 cm in circumference measured at 20 cm from the ground. |

Trunk:

| | |
|---|---|
| Trunk bark texture: | Fairly smooth with prominent lenticels becoming rough at the tree ages. |
| Trunk bark color: | Under color is RHS 156A. |
| Primary branches: | Branches are RHS 176A in color, overlaid with RHS 198D; a tree that is pruned using the standard open center system will annually produce upright shoots consisting entirely of one year wood, a typical example of which averages 1.7 m in length and 1.9 cm in diameter at the base, with lateral branches borne at crotch angles of 54 degrees. |
| Lenticels: | Moderate density, approximately 2.5 per square cm; typical examples of which measured 6 mm in length and 2.2 mm in width; RHS 177C in color, bordered with 198D. |
| Branch pubescence: | None. |
| New growth bark: | Color between RHS 178A and RHS 173B in sun; RHS 152D in shade. |
| Internodes: | Length averaging 22 mm on a one-year shoot. |

Leaves:

| | |
|---|---|
| Texture: | Glabrous. |
| Sheen: | Young leaves semi-glossy with a flat finish on the underside. |
| Length: | About 164 mm to 190 mm, averaging about 179 mm including the petiole. |
| Width: | About 30 mm to 45 mm, averaging about 39 mm. |
| Petiole: | Averaging 11.2 mm long and about 1.3 mm in diameter. |
| Margin: | Serrulate. |
| Margin undulation: | Slight to moderate. |
| Form: | Elliptic. |
| Apex: | Sharply acute, curved downward. |
| Base: | Broadly acute. |
| Venation: | Pinnate. |
| Glands: | |
| Number: | About 3 to 5, averaging about 3.8. |
| Position: | Located on the base of the leaf margin and petiole. |
| Size | Length averaging 1.1 mm and width averaging 1.0 mm. |
| Form: | Reniform. |
| Stipules: | None observed on mature leaves. |
| Leaf Color: | |
| Upper leaf surface: | Between RHS 147A and RHS 147B. |
| Lower leaf surface: | Between RHS 148A and RHS 148B. |
| Vein: | RHS 160B. |
| Pubescence | None. |

Flowers:

| | |
|---|---|
| Size: | Small size, typical flower measuring about 23.2 mm across. |
| Color: | |
| Dormant bud: | Between RHS 201A and RHS 201D. |
| Pink stage bud: | Between RHS 55A and RHS 55B. |
| Open flower: | Young open flowers RHS 55C, and becoming RHS 55C to RHS 55D at petal fall. |
| Petals: | Typically five petals per flower; obovate shape; averaging 13.7 mm long and 11.0 mm wide. RHS 55C in color. |
| Petal apex: | Rounded. |
| Petal base: | Acuminate. |
| Stamens: | |
| Number: | Variable, between 35 to 40, averaging 37.8. |
| Length. | Variable, between 11.5 mm to 14 mm, averaging 12.6 mm. |
| Filament color: | RHS 50D. |
| Anther color: | Between RHS 34A and RHS 34B. |
| Pistil: | |
| Number: | One. |
| Size: | Length between 12.7 and 14.8 mm, averaging about 13.7 mm. |
| Pistil color: | RHS 145A. |
| Ovary: | Dense pilose pubescence, and ellipsoid in shape. |
| Sepals: | |
| Number: | Five. |
| Color: | Between RHS 182A and RHS 152D in color, with light pubescence. |
| Shape: | Triangular, with a rounded apex. |
| Size: | Length averaging 5.1 mm, width averaging 3.9 mm. |
| Nectar cup color: | RHS 169C. |
| Pollen: | Abundant; RHS 13B in color. |
| Fragrance: | Very slight. |
| Bloom season: | Onset of bloom in 2004 on April 14; full bloom on April 23; starting petal fall on April 25; has a greater than average spread in the different stages of bloom development. |

Fruit:

| | |
|---|---|
| Size | Large, averaging about 6.8 cm long, 6.8 cm wide parallel to the suture and 6.4 cm wide perpendicular to the suture. |
| Typical weight: | 158 g |
| Form: | |
| Longitudinal section | Round. |
| Traverse section: | Nearly round, slightly ovate. |
| Suture: | Very shallow, extending form the base to apex. |
| Ventral surface: | Nearly smooth, very slightly lipped. |
| Base: | Round. |
| Apex: | Round. |
| Stem: | Average length of 10 mm and an average diameter of 5.2 mm. |
| Skin: | |
| Thickness: | Average. |
| Surface: | Regular with short pubescence. |
| Tenacity: | Average. |
| Astringency: | None. |
| Tendency to crack: | Very low. |
| Color: | Over color between RHS 46A to RHS 46B; under color RHS 16B. |
| Fruit Properties: | |
| Flesh color | RHS 15B becoming RHS 46A adjacent to the stone. |
| Flesh adhesion: | Freestone. |
| Juice: | Moderate. |
| Texture: | Firm, nearly nonmelting. |
| Fibers: | Not noticeable. |
| Ripens: | Between August 9 and August 25 at Cream Ridge, New Jersey. |
| Flavor: | Sweet, low acid. |
| Soluble solids: | 14.1%. |
| Aroma: | Very slight. |
| Eating quality: | Very good. |
| Keeping quality: | Excellent. Has held its flavor and firmness for at least 21 days in cold storage at 1° C. to 4° C. |
| Shipping quality: | Excellent. Fruit are very firm and soften slowly. No bruising or scaring disorders have been observed. |
| Usage | Desert. |
| Market: | Local and long distance. |

-continued

| | |
|---|---|
| Productivity: | Excellent. Tree has produced a crop in 10 out of 11 years, and a full crop in 9 out of 11 years at Cream Ridge, New Jersey. |

Stone:

| | |
|---|---|
| Type: | Freestone. |
| Form: | Obovate. |
| Base: | Narrow. |
| Apex: | Narrow. |
| Surface: | Chains of pits forming grooves. |
| Dorsal ridge: | Medium, narrow, and medium deep lines. |
| External Color: | RHS 177C overlaid with RHS 183C near the stem end, especially along the suture. |
| Internal color when cracked: | Between RHS 165C and RHS 165D. |
| Cavity surface color: | RHS 165C. |
| Average stone weight: | 4.4 g. |
| Average stone wall thickness: | 4.5 mm. |
| Size: | Averages about 31 mm long, 22 mm wide parallel to the dorsal ridge, and 16 mm wide perpendicular to the dorsal ridge. |
| Tendency to split: | None observed. |
| Kernel: | |
| Form: | Ovate. |
| Skin color: | RHS 16D. |
| Vein color: | Between RHS 163C and RHS 165B. |
| Viability: | Yes, embryo developed. |
| Size | Averages about 17 mm long, 11.6 mm wide and 5.7 mm thick. |

Plant/fruit disease and pest resistance/susceptibility: No atypical resistances/susceptibilities have been noted under normal cultural practices.

We claim:

1. A new and distinct variety of peach tree, substantially as herein shown and described.

* * * * *